(12) United States Patent
Lee

(10) Patent No.: US 6,551,431 B2
(45) Date of Patent: Apr. 22, 2003

(54) INDIVIDUALLY WRAPPED ABSORBENT ARTICLE AND METHOD AND APPARATUS FOR ITS PRODUCTION

(75) Inventor: Colin Lee, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 219 days.

(21) Appl. No.: 09/740,099

(22) Filed: Dec. 18, 2000

(65) Prior Publication Data

US 2001/0004688 A1 Jun. 21, 2001

Related U.S. Application Data (62) Division of application No. 08/968,446, filed on Nov. 12, 1997.

(51) Int. Cl.[7] ............................ B65H 45/18; B65H 45/30
(52) U.S. Cl. ....................... 156/226; 156/227; 156/251; 156/443; 156/515; 156/566
(58) Field of Search ................................. 156/443, 461, 156/464, 465, 251, 269, 515, 552, 556, 566, 226, 227; 493/405, 444; 53/116, 117, 513, 520, 203

(56) References Cited

U.S. PATENT DOCUMENTS

| | | | |
|---|---|---|---|
| 4,735,316 A | * | 4/1988 | Froidh et al. ............... 206/438 |
| 5,176,615 A | * | 1/1993 | Munsch ....................... 493/427 |
| 6,251,209 B1 | * | 6/2001 | Johnson ....................... 156/201 |

FOREIGN PATENT DOCUMENTS

| WO | WO 91/18574 | 12/1991 |
|---|---|---|

\* cited by examiner

*Primary Examiner*—Richard Crispino
*Assistant Examiner*—Cheryl N. Hawkins
(74) *Attorney, Agent, or Firm*—Patterson, Thuente, Skaar & Christensen, LLC (57) ABSTRACT

An individually wrapped absorbent article such as a sanitary napkin which is simple, compact, sanitary, and easy to unwrap for use and to dispose of after use. The absorbent article avoids the need for a separate peel strip and pouch because it is provided with a wrapper that can be folded into a pouch. Substantially the entire backsheet of the absorbent article directly faces the wrapper and is secured to it to form an assembly. In the case of a winged or tabbed type absorbent article, this configuration obviates the need for a separate peel strip to cover the garment adhesive located on the wings or tabs. The assembly is wrapped by folding the lateral flaps thereof longitudinally over one another to enclose the article to prevent the garment adhesive from becoming contaminated. The package is then tri-folded laterally to form an e-shaped pouch. Wrapping and folding can be performed by an in-line process that uses simple equipment and that does not require reversal in the direction of article conveyance.

11 Claims, 7 Drawing Sheets

INDIVIDUALLY WRAPPED ABSORBENT ARTICLE AND METHOD AND APPARATUS FOR ITS PRODUCTION

CROSS-REFERENCE TO RELATED APPLICATION

This application is a divisional of U.S. Ser. No. 08/968,446 filed on Nov. 12, 1997, the benefit of which is now claimed pursuant to 35 USC § 120.

BACKGROUND OF THE INVENTION

1. Field of the Invention

This invention relates to absorbent articles such as sanitary napkins, pantyliners, incontinent products or the like and, more particularly, relates to an individually wrapped absorbent article in which the article is releasably secured to a peel strip and folded and sealed to form a package. The package is wrapped and folded to form a pouch for storing and transporting the absorbent article. The invention additionally relates to a method of wrapping and folding an individually wrapped absorbent article of the aforementioned type and to an apparatus for practicing the method.

2. Discussion of the Related Art

Absorbent articles are well known for absorbing and retaining bodily fluids such as urine, menstrual fluids, blood, etc. Typical of these absorbent articles are sanitary napkins, pantyliners, incontinent products, and the like. The problems addressed by the art will be discussed primarily with reference to sanitary napkins, it being understood that pantyliners, incontinent products, and other absorbent articles also exhibit some or all of these problems.

The two types of sanitary napkins currently in use are a wingless or tabless type that is generally rectangular in shape and a winged or tabbed type that has wings or tabs (hereinafter "wings") extending laterally beyond the lateral edges of the main body of the napkin in a longitudinally central portion thereof. The typical sanitary napkin of either type comprises an absorbent core encased or enclosed within an envelope or sheath that includes a topsheet, also referred to as a "cover," and a backsheet, also referred to as a "baffle." The topsheet is designed to face the user and is liquid-permeable to permit liquid passage to the absorbent core where the liquid is retained. The backsheet is liquid-impermeable. A strip of garment-attachable adhesive is secured on the outer surface of the backsheet to permit releasable or detachable securement of the napkin to a user's undergarment. In the case of a winged or tabbed type napkin, additional adhesive strips or patches are secured to the bottom surface of the wings to permit securement of these wings to the user's undergarment. The adhesive strips can be transferred to the napkins by applying the adhesive to the releasable peel strips, and the adhesive is then transferred to the napkins when the peel strip is attached to the backsheet or baffle. The peel strip protects the adhesive from contamination until the napkins are ready for use, at which time the user removes the peel strips.

Individually wrapped sanitary napkins are desirable for a variety of reasons. For instance, they are compact (e.g., they can be conveniently carried in a consumer's pocket or purse), they prevent the sanitary napkins and the liners from becoming contaminated or soiled prior to use, and used napkins can be disposed of using the pouches or other wrapping materials. Individually wrapped sanitary napkins are disclosed, for example, in U.S. Pat. No. 3,973,567 to Srinivasan et al. (the Srinivasan patent); U.S. Pat. No. 4,556,146 to Swanson et al. (the Swanson patent); and U.S. Pat. No. 5,413,568 to Roach et al. (the Roach patent). All of these patents disclose a sanitary napkin having a backsheet portion adhered to a liner or peel strip that also forms at least part of a wrapper for the napkin. The Srinivasan and Swanson patents disclose individually wrapped wingless or tabless disposable sanitary napkins, whereas the Roach patent discloses an individually wrapped winged or tabbed sanitary napkin.

Conventional individually wrapped sanitary napkins such as those disclosed in the Srinivasan, Swanson, and Roach patents exhibit several drawbacks and disadvantages. For instance, they are relatively difficult to open. In the case of the Swanson patent, the wrapper faces and receives the backsheet portion of the napkin so as to present longitudinal and lateral flaps surrounding the napkin. The napkin and affixed wrapper are then tri-folded as a unit. The lateral edges of the longitudinal flaps are frangibly sealed along their entire length to prevent napkin contamination. These seals must be broken when unwrapping the assembly. This seal breaking requirement hinders unwrapping. In addition, the wrapper is ill-suited for disposal of a used napkin because it is not substantially larger than the napkin.

Napkins of the tabbed or winged type also exhibit additional wrapping challenges. For instance, in the Roach patent, a tabbed or winged type napkin is disclosed which has a backsheet that is releasably adhered to a wrapper similar to the manner in which the Swanson's backsheet is adhered to the corresponding wrapper. However, the ends of the wings extend beyond the lateral edges of the wrapper. The exposed wings are folded longitudinally over the topsheet of the body of the napkin so that the wings are aligned and adjacent to the topsheet of the napkin with their ends facing the longitudinal centerline of the napkin and with their adhesive patches or strips facing upwardly. The wings must be covered with at least one and possibly two separate or dedicated pieces of release liner to protect the adhesive patches on the wings. The additional release liner(s) must be individually removed by the consumer prior to napkin use. This extra step is inconvenient at best and also presents the consumer with at least one additional piece of waste material for disposal. Moreover, because the wrapper is not substantially wider than the body of the napkin, it is rather difficult for the consumer to use the wrapper to dispose of a used napkin.

Another problem associated with conventional individually wrapped sanitary napkins is that production is hindered because wrapping and folding requires a separate process and apparatus and/or because the wrapping and folding operations cannot be performed in-line. Wrapping and folding instead are performed via rather large and complex drum, roll, and striker blade configurations that require at least one and usually several changes in the direction of napkin conveyance during the wrapping and folding processes. Examples of typical processes exhibiting these disadvantages can be found in U.S. Pat. No. 3,635,462 to Joa; U.S. Pat. No. 4,701,156 to Larsonneur; and U.S. Pat. No. 5,176,615 to Munsch.

SUMMARY OF THE INVENTION

It is therefore a principal object of this invention to provide an improved individually wrapped absorbent article that is compact and easy to unwrap.

Another object of this invention is to provide an absorbent article that meets the first principal object of this invention and that, in its fully wrapped state, is sanitary but still easy to unwrap.

Still another object of this invention is to provide an individually wrapped absorbent article that meets at least the first principal object and that does not require a separate peel strip as well as a wrapper.

Yet another object of this invention is to provide an individually wrapped absorbent article that meets at least the first principal object and that can be easily disposed of using the supplied wrapper.

In accordance with a first aspect of this invention, these objects are achieved by providing an individually wrapped absorbent article containing package that comprises an absorbent article and a wrapper. The absorbent article has first and second major mutually opposed faces, and the wrapper has an absorbent article-receiving surface to which at least a portion of the first face of the absorbent article is releasably secured to form an assembly. The assembly has a longitudinal centerline, a lateral centerline, and a perimeter. The perimeter is formed from a pair of opposed lateral edges disposed on opposite sides of the longitudinal centerline and a pair of opposed longitudinal ends disposed on opposite sides of the lateral centerline. The lateral edges are wrapped over the second face of the absorbent article and sealed to form a package.

Preferably, in order to fully-seal the package, a pair of opposed longitudinal ends of the package are each sealed by binding the wrapper to itself.

This invention is applicable to both winged absorbent articles such as winged sanitary napkins and the like and to wingless or tabless absorbent articles such as wingless sanitary napkins, pantyliners, and the like.

Another object of this invention is to provide a package which meets one or more of the foregoing objects and which is folded, rolled, or otherwise manipulated to form a pouch. Preferably, the pouch includes a central portion and first and second longitudinal flaps. The first longitudinal flap is aligned and adjacent to the central portion, and the second longitudinal flap is aligned and adjacent to the first longitudinal flap. The second longitudinal flap preferably is releasably secured to the first longitudinal flap.

Another principal object of this invention is to prove an individually-wrapped winged sanitary napkin that does not require separate peel strips for the wings of the napkin.

In accordance with another aspect of this invention, this object is achieved by providing an assembly formed from an absorbent article and a wrapper. The absorbent article has first and second major mutually opposed faces, includes a main absorbent body having opposed lateral edges, and includes a pair of wings extending laterally outward from the opposed lateral edges. At least a portion of the first face of the absorbent article is releasably secured to an article-receiving face of the wrapper to form the assembly. In order to protect the garment adhesive on the wings while eliminating the need for a separate peel strip on the wings, the portion of the first face that is secured to the wrapper includes at least part of the absorbent body and at least part of each of the wings.

Preferably, the assembly is wrapped to form a package and then folded to form a pouch as discussed above in conjunction with the first primary object.

Another principal object of this invention is to provide a relatively simple and expedient method of wrapping and folding an assembly formed from an absorbent article and a wrapper to which the absorbent article is releasably secured.

Preferably, the assembly has a longitudinal centerline and a perimeter formed from a pair of laterally-opposed side flaps disposed on opposite sides of the longitudinal centerline and a pair of opposed longitudinal ends. This assembly is wrapped and folded to form a pouch by folding the side flaps longitudinally onto the second face of the absorbent article to form a package, and then folding the package laterally to form a pouch. The step of folding the package laterally preferably comprises folding a first longitudinal flap of the package over a central portion of the package so that the first longitudinal flap is aligned and adjacent to the central portion, then folding a second longitudinal flap over the first longitudinal flap so that the second longitudinal flap is aligned and adjacent to the first longitudinal flap. The first and second longitudinal flaps are then releasably secured to one another.

Another object of this invention is to provide a method which meets the second principal object of this invention and which wraps and folds the absorbent articles in an in-line fashion.

In accordance with still another aspect of this invention, this object is achieved by driving a first reciprocating pusher into the package at a location in the vicinity of a lateral fold-line connecting the central portion to the first longitudinal flap, and by driving a second reciprocating pusher into the package at a location in the vicinity of a lateral fold-line connecting the central portion to the second longitudinal flap.

Yet another principal object of this invention is to provide an improved system for wrapping and folding individually wrapped absorbent articles.

In accordance with still another aspect of this invention, this object is achieved by providing a first conveyor which is adapted to convey assemblies comprising a wrapper and an absorbent article secured to the wrapper to the system, a second conveyor which is adapted to convey pouches from the system, and first and second pusher assemblies. The first pusher assembly comprises a vertically reciprocating pusher which is adapted to receive the assemblies from the first conveyor and to partially-fold the assemblies. The second pusher assembly is a horizontally reciprocating pusher located in a vertically-spaced relationship with respect to the first conveyor and the first pusher and which is adapted to receive the assemblies from the first pusher and to further fold the assemblies to form the pouches.

Preferably, the first and second pushers are slotted to permit application of an adhesive to the assemblies without interference from the first and second pushers.

Other system components preferably include 1) a package former which releasably secures absorbent articles to a continuous sheet of wrapper material to form the packages, 2) a longitudinal folder which is located downstream of the package former and which folds the continuous sheet longitudinally to form wrapped packages in which lateral edges of the continuous sheet are positioned laterally inwardly of lateral edges of the packages, and 3) a cutter which is located between the longitudinal folder and the first conveyor and which cuts the continuous sheet between the packages.

Other objects, features, and advantages of the present invention will become apparent to those skilled in the art from the following section entitled Detailed Description of the Preferred Embodiment and from the accompanying drawings. It should be understood, however, that the Detailed Description and specific drawings, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWINGS

A preferred exemplary embodiment of this invention is illustrated in the accompanying drawings in which like reference numerals represent like parts throughout, and in which.

DETAILED DESCRIPTION OF THE PREFERRED EMBODIMENT

Pursuant to this invention, an individually wrapped absorbent article such as a sanitary napkin, a pantyliner, an incontinent device, or the like is provided which is simple, compact, sanitary, and easy to unwrap for use and to dispose of after use. The absorbent article does not require a separate peel strip or liner and/or pouch because it is provided with a releasable wrapper which serves as a wrapper as well as a pouch. Substantially the entire backsheet or baffle of the absorbent article directly faces the upper surface of the wrapper and is secured to it by a releasable adhesive to form a combination or assembly. In the case of a winged or tabbed type absorbent article, this configuration obviates the need for one or more additional peel strips for the wings or tabs. The assembly is wrapped to form a package and prevent article contamination by longitudinally folding side flaps of the wrapper. The wrapped package is then tri-folded laterally to form an e-shaped pouch. Wrapping and folding can be performed via an in-line process that uses simple equipment and that does not require reversal in the direction of napkin conveyance.

This invention is applicable to a variety of individually wrapped absorbent articles including sanitary napkins, pantyliners, incontinent products, and the like. It is particularly well applicable to sanitary napkins for absorbing and retaining menstrual fluids. The invention therefore will be discussed primarily in conjunction with sanitary napkins, it being understood that it applies to other absorbent articles as well.

Figure 1:
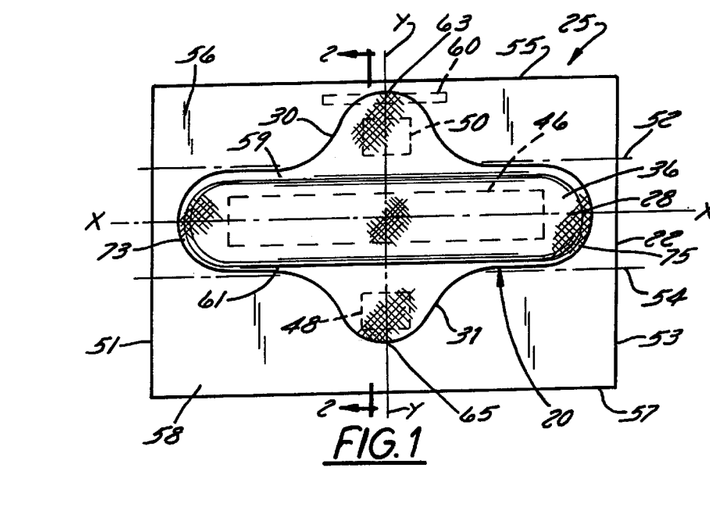
FIG. 1 is a top plan view of an assembly constructed in accordance with a first preferred embodiment of the present invention and formed from an absorbent article and a wrapper.
Figure 2:
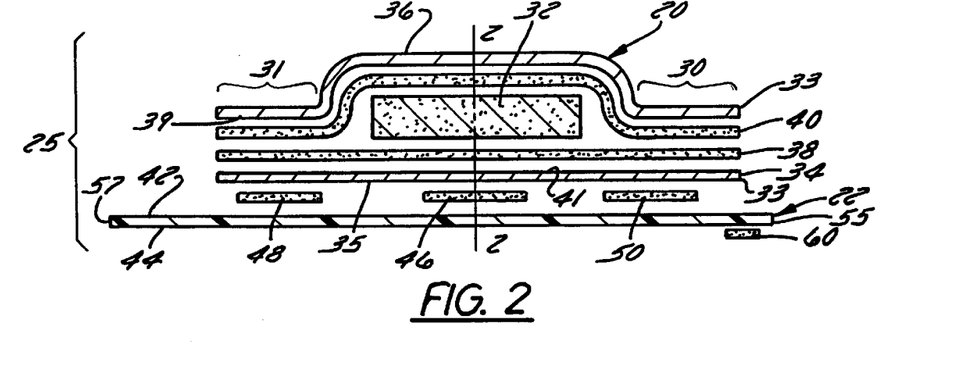
FIG. 2 is a partially exploded sectional elevation view taken generally along the lines 2—2 in FIG. 1.
Figure 3:
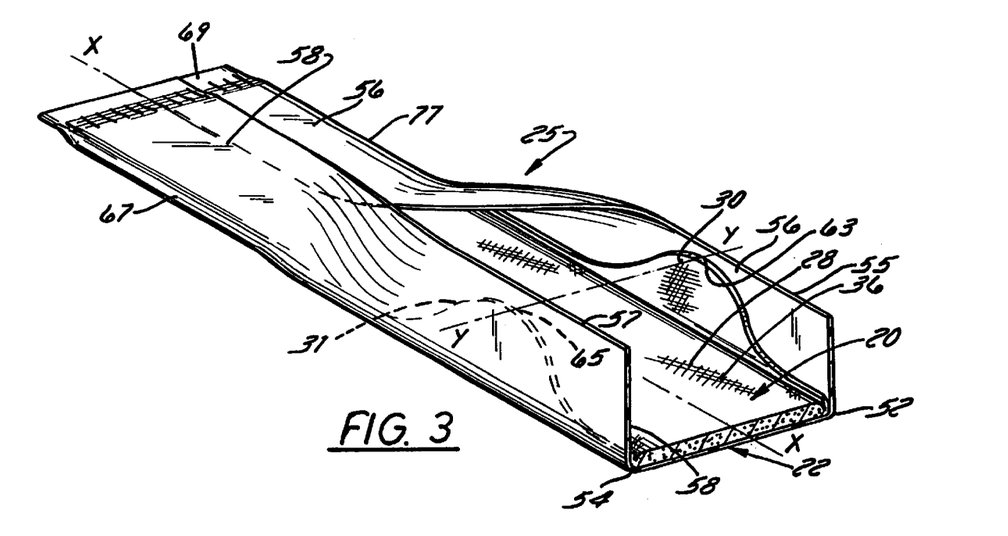
FIG. 3 is a perspective view of the absorbent article and wrapper assembly shown in of FIG. 1 and illustrating the absorbent article in a partially-wrapped state.
Figure 4:
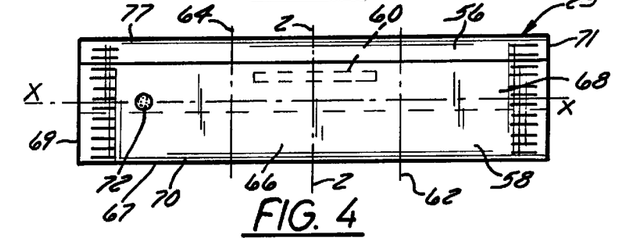
FIG. 4 is a plan view of the combination absorbent article and wrapper shown in FIG. 1 and illustrating the assembly in a state in which it is fully wrapped to form a package.
Figure 5:
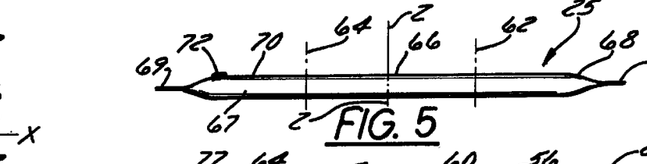
FIG. 5 is a side elevation view of the package of FIG. 4.
Figure 6:
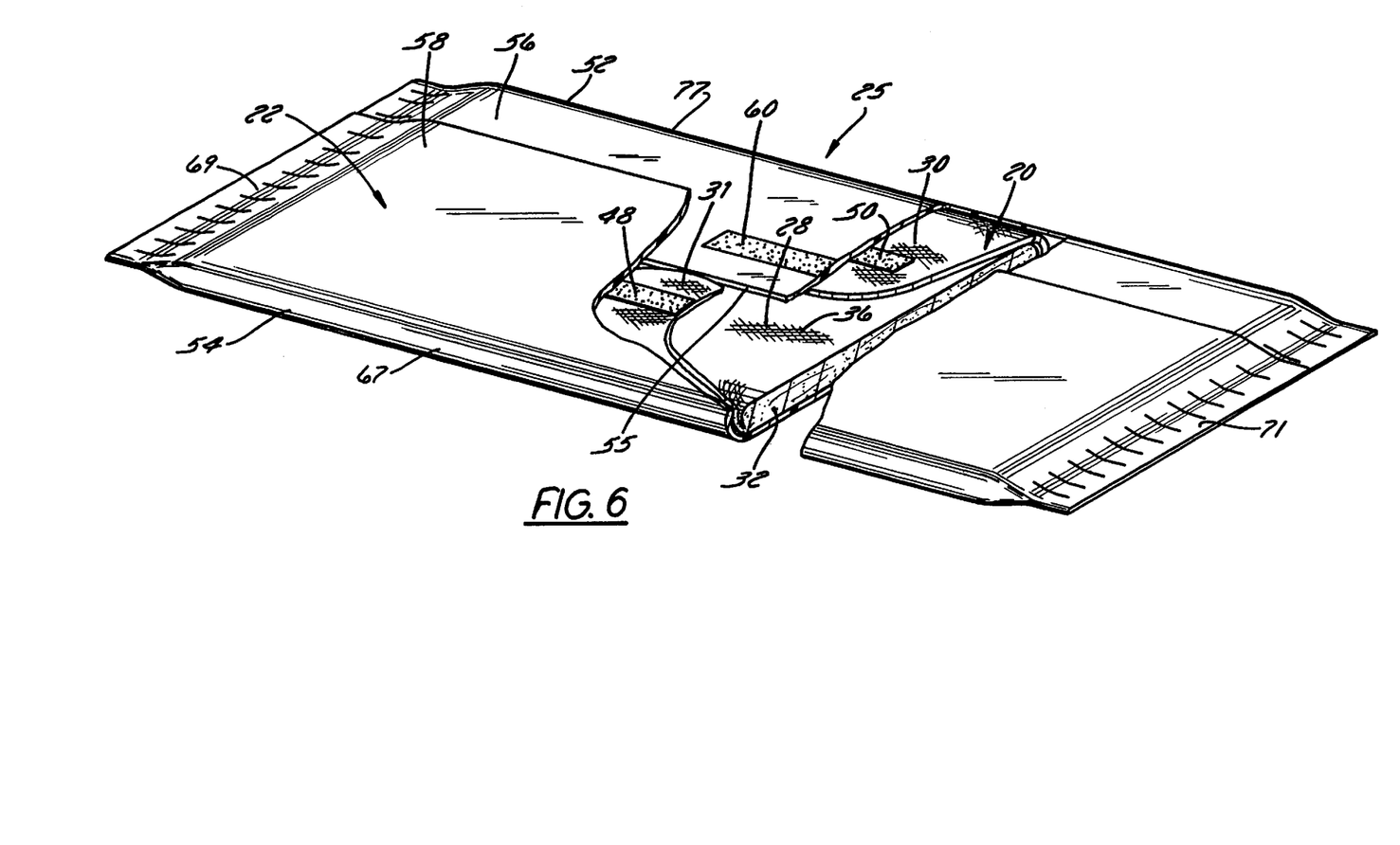
FIG. 6 is a partially cut away perspective view of the package of FIGS. 4 and 5.
Figure 7:
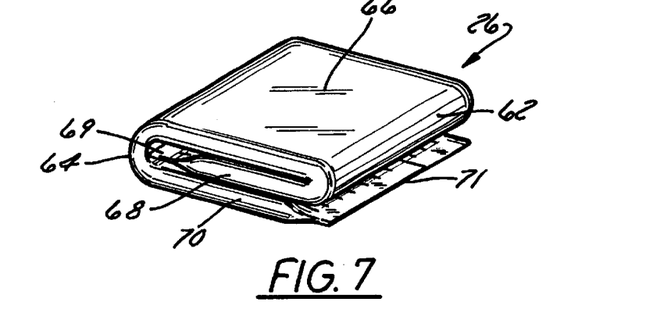
FIG. 7 is a perspective view of a pouch formed by folding the package of FIGS. 4–6.

A sanitary napkin 20 is illustrated in FIGS. 1–3 which is releasably secured by adhesion to a wrapper 22 to form an assembly 24. The assembly 24 is folded and sealed to form a package 25 which is best seen in FIGS. 4–6, and the wrapped package is then tri-folded to form a generally e-shaped pouch 26 which is best seen in FIG. 7.

Referring initially to FIG. 1, the sanitary napkin 20 of this embodiment is a winged or tabbed product having a main absorbent body 28 and a pair of laterally-opposed wings or tabs 30 and 31, hereafter referred to as simply "wings". Each of the wings 30 and 31 extends laterally outward from a longitudinally central portion of a respective one of the lateral edges of the main absorbent body 28. As is well known in the art, the wings 30 and 31 are designed for detachable securement to the outer surface of the undergarment of the consumer.

Referring to FIG. 2, the sanitary napkin 20 includes an absorbent core 32 and an envelope 33 encasing the absorbent core 32. The absorbent core 32 may be formed from any suitable absorbent material such as pulp, cellulose wadding, air-felt, layers of tissue paper, superabsorbent materials, or combinations thereof The envelope 33 includes a liquid-impervious backsheet or baffle 34 which is disposed below the absorbent core 32 and a liquid-permeable topsheet or cover 36 which is positioned above the absorbent core 32. The topsheet 36 is configured to face the user's body and functions to permit liquids to pass through it for retention by the absorbent core 32. The backsheet 34 has a back face 35 which is configured to be releasably secured to the wrapper 22 by three garment adhesive strips or patches 46, 48, and 50. The garment adhesive strips 46, 48, and 50 could be formed from any suitable adhesive and preferably are formed from a pressure-sensitive adhesive of the type commonly used in the art. It should be noted that one or two wide adhesive strips could be used in place of three narrower adhesive strips 46, 48, and 50. Once the wrapper 22 is removed from the napkin 20, the garment adhesive strips 46, 48, and 50 remain with the napkin 20 and function to attach and hold the napkin 20 in position on the inner surface of the user's undergarment. The topsheet 36 is secured to the backsheet 34 by a construction adhesive 38 located on the inner surface 39 of the topsheet 36 and a bodyside layer of construction adhesive 40 on the inner or front face 41 of the backsheet 34. This construction adhesive 40 could be eliminated in favor of a thermal bond if desired or by other bonding techniques known to those skilled in the art, such as ultrasonics.

The sanitary napkin 20 per se is conventional. However, its relationship with the wrapper 22 and the package pouch 26 formed by wrapping and folding the assembly 24 (see FIG. 7) formed by the napkin 20 and wrapper 22 combination is not. This relationship will now be explained.

Referring again to FIG. 2, the releasable wrapper 22 could conceivably comprise a multi-ply or multi-component arrangement but preferably comprises a single sheet that serves as both a wrapper and as a releasable peel strip. The wrapper 22 may be formed from any suitable thermoplastic such polyethylene or polypropylene, with polyethylene being preferred. The wrapper 22 has first and second opposed major surfaces 42, 44 respectively, with the first or inwardly-orientated surface 42 preferably being coated with a suitable release material to facilitate separation from the adhesive strips 46, 48, and 50. The adhesive strips 46, 48, and 50 could take many configurations so long as they secure both the main absorbent body 28 and the wings 30 and 31 to the wrapper 22. The adhesive strips 46, 48, and 50 permit securement of the main absorbent body 28 and the wings 30 and 31 to the user's undergarment after the napkin 20 is peeled away and removed from the wrapper 22. The three adhesive strips 46, 48, and 50 are relatively long narrow strips. The first or middle strip 46 is aligned along the longitudinal centerline X—X of the main absorbent body 28 (FIG. 1) and extends a substantial percentage of the longitudinal length of the napkin 20. For example, the adhesive strips 46, 48, and 50 can extend about 50% to about 99% of the full length of the napkin 20. The second and third strips 48 and 50, respectively, are each disposed beneath a generally central portion of the respective wings 30 and 31. It is important to note that the second and third adhesive strips 48 and 50 serve to secure the wings 30 and 31 to the wrapper 22. This obviates the need to fold the wings 30 and 31 back over the main absorbent body 28 and to protect the adhesive strips 48 and 50 via a separate peel strip.

Referring again to FIG. 1, the releasable wrapper 22 has a perimeter defined by a pair of longitudinal ends 51 and 53 disposed on opposite sides of the lateral centerline Y—Y and a pair of lateral edges 55 and 57 disposed on opposite sides of the longitudinal centerline X—X. Preferably, the lateral edges 55 and 57 of the wrapper 22 extend outwardly beyond the respective lateral side margins of the sanitary napkin 20 so that lateral spaces are formed between outermost lateral ends 63 and 65 of the wings 30 and 31 and the edges of the wrapper 22. The lateral edges 55 and 57 of the wrapper 22 preferably extend about 1.5" to 2.5", and even more preferably about 2.0", beyond the corresponding lateral edges 59 and 61 of the main absorbent body 28. The lateral edges 55 and 57 of the wrapper 22 also extend between about 0.25" and 0.75", and even more preferably about 0.5", beyond the ends 63 and 65 of the wings 30 and 31. The longitudinal ends 51 and 53 of the wrapper 22 similarly extend beyond longitudinal ends 73 and 75 of the napkin 20. This configuration not only facilitates securement of the napkin 20 to the wrapper 22 but also ensures that enough wrapper material is available to permit disposal of a used napkin 20 in it.

The combination of the napkin 20, being releasably secured to the wrapper 22, is folded and sealed to form a package 25 (FIGS. 3–6). The package 25 is then folded to provide a sanitary, compact, easy to handle and easy to unwrap pouch 26 (see FIG. 7).

Specifically, referring to FIG. 3, the wrapper 22 is folded longitudinally about the napkin 20 along two longitudinally-extending fold lines 52 and 54, so that a side flap 56 and a side flap 58 extend laterally from the opposed lateral edges 55 and 57 of the wrapper 22. The side flaps 56 and 58 rest on the topsheet 36 of the napkin 20 after folding as seen in the left half of FIG. 3. This wrapping protects lateral edges 67 and 77 of the napkin 20 from contamination and obviates the need to seal the edges of the package 25, thereby facilitating production and also facilitating use, to the extent that there is no need to break a seal running the length of the package 25 when unwrapping the napkin 20. Preferably, the longitudinal fold lines 52 and 54 are coextensive with the longitudinal sides or edges 59 and 61 of the absorbent body 28 and are located such that the side flap 58 overlaps the other side flap 56 in the vicinity of the longitudinal centerline X—X of the package 25 as seen in FIG. 4, thereby completely covering the napkin's topsheet 36. The side flaps 56 and 58 may be secured to one another by adhesive 60 in the form of one or more adhesive dots or strips (see FIGS. 2 and 4) to facilitate subsequent folding and to provide a more compact package 25. However, there is no need to apply the adhesive strip 60 along the entire length of the overlap even in those instances in which the adhesive strip 60 is utilized.

Ends 69 and 71 of the package 25 also are preferably sealed as seen in FIGS. 4–6 to fully enclose the napkin. The wrapped package 25 is folded laterally (i.e., parallel to the lateral centerline Y—Y in FIGS. 4 and 5) about laterally-extending fold lines 62 and 64 to form a pouch 26 (FIG. 7) having a central portion 66 and first and second longitudinal flaps 68 and 70. The first flap 68 is positioned adjacent to and below the central portion 66, and the second flap 70 is positioned adjacent to and below the first flap 68, as illustrated in FIG. 7, to form a generally e-shaped pouch. The second flap 70 is frangibly secured to the first flap 68 to prevent the pouch 26 from unintentionally unfolding. The securement could be accomplished by use of an adhesive 72 (best seen in FIGS. 4 and 5), such as dots or a strip of adhesive tape extending from the outer end 69 of the second flap 70 to the inner end of the first flap 68 forward by the fold line 62. As illustrated, the securement is achieved by application of an adhesive spot 72 (hereafter a "patch") of a pressure sensitive adhesive positioned between the first and second flaps 68 and 70 at a location near the outer end 69 of the second flap 70.

The finished wrapped and folded pouch 26 is extremely sanitary because the napkin 20 is essentially completely sealed from the environment. The pouch 26 also is quickly and readily opened and unwrapped simply by pulling the second flap 70 away from the first flap 68, against the relatively small resistance of the frangible adhesive patch 72. The side flaps 58 and 56 are then unfolded against the relatively slight resistance of the frangible adhesive strip 60. The napkin 20 can now be peeled away from the wrapper 22 simply by grasping one end of the napkin 20 and pulling it longitudinally with respect to the wrapper 22. There is no need to touch any sanitary portions of the napkin 20. Nor is there any need to remove separate peel strips that otherwise would be required to cover the adhesive strips 48 and 50 positioned over the wings 30 and 31. The napkin 20 is now ready for attachment to an undergarment. After use, the napkin 20 can be conveniently disposed of by simply wrapping it in the wrapper 22. This wrapping and subsequent disposal are facilitated by the fact that the wrapper 22 is substantially larger than the napkin 20 in both the longitudinal and lateral directions. There is also no need to open a separate pouch to remove the napkin for use or to force a used napkin in a separate preformed pouch during disposal. Unwrapping and disposal thereby are significantly facilitated when compared to many prior art products.

Figure 8:
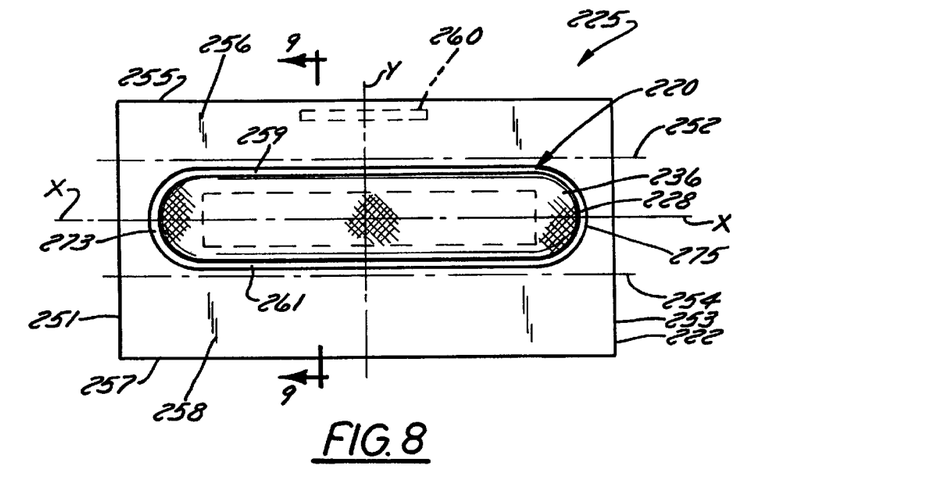
FIG. 8 is a top plan view of an assembly constructed in accordance with a second preferred embodiment of the present invention and formed from an absorbent article and a wrapper.
Figure 10:
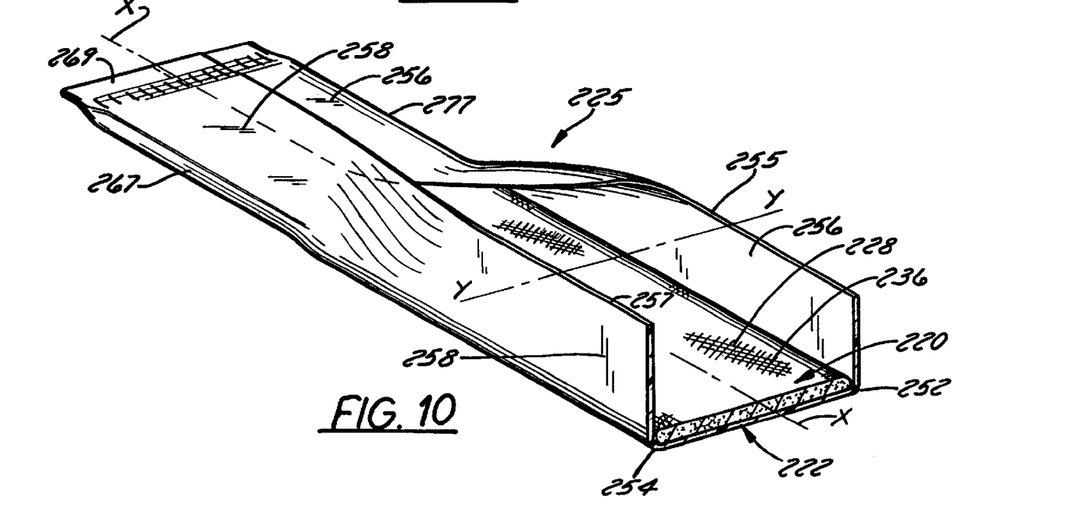
FIG. 10 is a perspective view of the combination absorbent article and wrapper shown in FIG. 8 and illustrating the absorbent article in a partially-wrapped state.

The invention is also applicable to wingless absorbent articles such as a wingless sanitary napkin 220 illustrated in FIG. 8. The napkin 220 is releasably secured by adhesion to a wrapper 222 to form an assembly 224. The assembly 224 is folded and sealed to form a package 225 which is best seen in FIG. 10, and the wrapped package is then tri-folded to form a generally e-shaped pouch.

Figure 9:
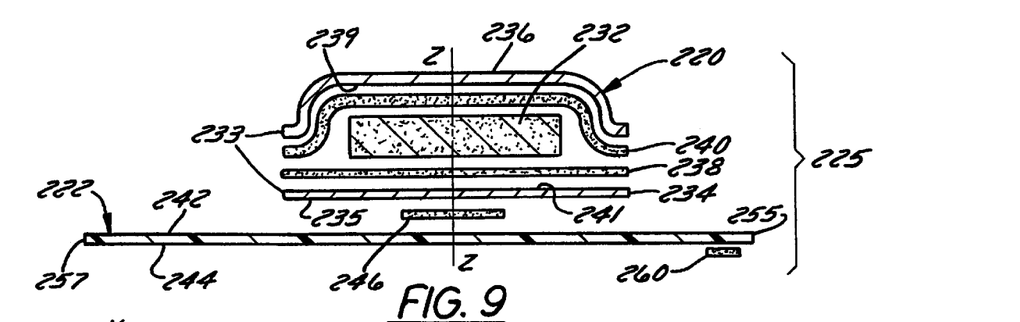
FIG. 9 is a partially exploded sectional elevation view taken generally along the lines 9—9 in FIG. 8.

Referring to FIG. 8, the sanitary napkin 220 of this embodiment has a main absorbent body 228 that is generally rectangular in shape and that has a pair of opposed lateral edges 259 and 261 and a pair of opposed longitudinal ends 273 and 275. "Generally rectangular" as used herein should be construed to encompass oval shapes, hourglass shapes, and the like in addition to encompassing a true rectangular shape. The releasable wrapper 222 has a first or article-receiving surface 242, a second surface 244 (best seen in FIG. 9), and a perimeter defined by opposed longitudinal ends 251 and 253 disposed on opposite sides of a lateral centerline Y—Y and opposed lateral edges 255 and 257 disposed on opposite sides of a longitudinal centerline X—X. Preferably, the lateral edges 255 and 257 of the wrapper 222 extend about 1.5" to 2.5", and even more preferably about 2.0", beyond the corresponding lateral edges 259 and 261 of the main absorbent body 228. As discussed above in conjunction with the first embodiment, this configuration not only facilitates securement of the napkin 220 to the wrapper 222, but also ensures that enough wrapper material is available to permit disposal of a used napkin 220 in the wrapper.

Referring again to FIG. 9, the sanitary napkin 220 includes an absorbent core 232 and an envelope 233 encasing the absorbent core 232. The envelope 233 includes a liquid-impervious backsheet or baffle 234 which is disposed below the absorbent core 232 and a liquid-permeable topsheet or cover 236 which is positioned above the absorbent core 232. The topsheet 236 is configured to face the user's body and functions to permit liquids to pass through it for retention by the absorbent core 232. The backsheet 234 has a back face 235 which is configured to be releasably secured to the first or article receiving surface 242 of the wrapper 222 by a garment adhesive 246 which could take the form a single strip as illustrated or which could be replaced by two or more discrete strips or patches. The topsheet 236 is secured to the backsheet 234 by a construction adhesive 238 located on an inner surface 239 of the topsheet 236 and a bodyside layer of construction adhesive 240 on the inner or front face 241 of the backsheet 238. As with the embodiment of FIGS. 1–7, this construction adhesive 240 could be eliminated in favor of a thermal bond if desired or by other bonding techniques known to those skilled in the art, such as ultrasonics.

As with the first embodiment, the assembly 224 is wrapped to form a package and may additionally be folded to form a pouch. Referring to FIG. 10, a package 225 is formed by folding the wrapper 222 longitudinally about the napkin 220 along two longitudinally-extending fold lines 252 and 254, respectively, so that a side flap 256 and a side flap 258 extend laterally from the opposed lateral edges 255 and 257 of the wrapper 222. The side flaps 256 and 258 rest on the topsheet 236 of the napkin 220 after folding as seen in the left half of FIG. 10. As discussed above in conjunction with the first embodiment, this wrapping protects the lateral edges 267 and 277 of the napkin 220 from contamination and obviates the need to seal the edges of the package 225, thereby facilitating production and also facilitating use, to the extent that there is no need to break a seal running the length of the package 225 when unwrapping the napkin 220. Preferably, the longitudinal fold lines 252 and 254 are coextensive with the longitudinal sides or edges 259 and 261 of the napkin 220 and are located such that the side flap 258 overlaps the other side flap 256 in the vicinity of the longitudinal centerline X—X of the package 225, thereby completely covering the napkin's topsheet 236. The side flaps 256 and 258 may be secured to one another by adhesive 260 in the form of one or more adhesive dots or strips (see FIG. 9) to facilitate subsequent folding and to provide a more compact package 225. Ends 269 and 271 of the package 225 also are preferably sealed to fully enclose the napkin as seen in conjunction with the end 269 half of FIG. 10.

The package 225 preferably is folded longitudinally to produce an e-shaped pouch. This pouch is identical in appearance to the pouch 26 of the first embodiment and, accordingly, need not be discussed in detail.

The above-described individually wrapped sanitary napkins 20 or 220, as well as similarly configured absorbent articles, could be wrapped and folded by a variety of processes, including manually. It is preferred, however, that the wrapping and folding take place automatically on an in-line process that does not require interruption of assembly conveyance or sudden reversal in the direction of assembly conveyance. One such process and an apparatus for its practice now will be detailed in conjunction with the winged sanitary napkin 20 of the first embodiment, it being understood that the same or virtually the same process and apparatus could be used to wrap and fold the wingless sanitary napkin 220 of the second embodiment as well as other individually wrapped absorbent articles such as pantyliners, incontinent products, or the like.

Figure 11:
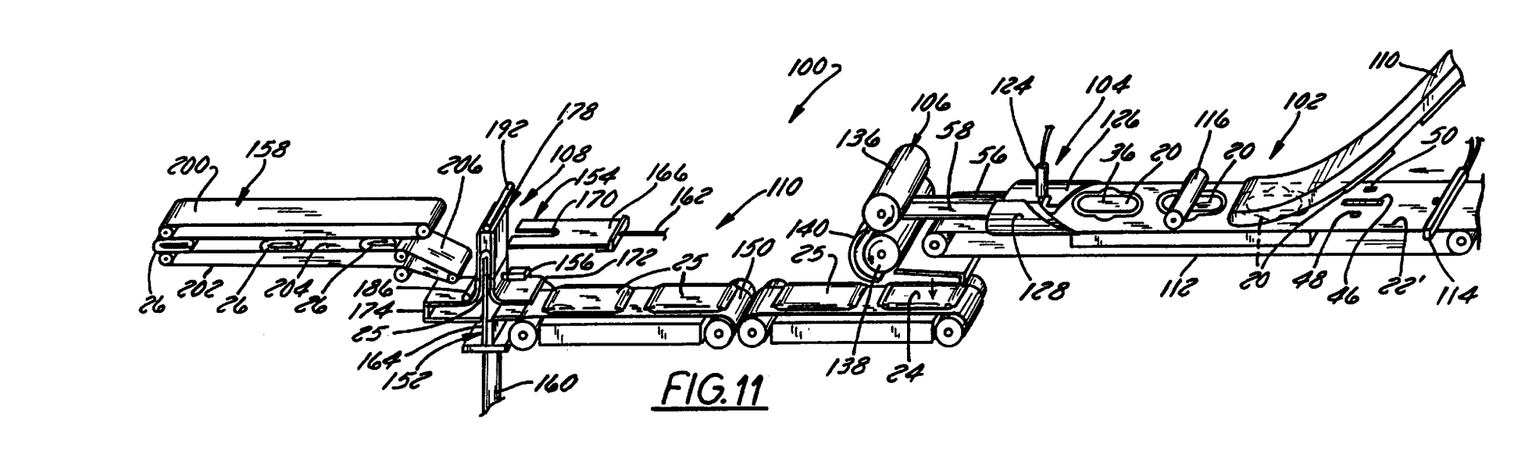
FIG. 11 is a partially schematic perspective view of a system for combining an absorbent article and wrapper to form an assembly, folding the assembly into a package, and then forming the package into a pouch.

Referring now to FIGS. 11 through 15, a wrapper/folder system 100 is illustrated which forms assemblies 24 from sanitary napkins 20 and wrappers 22, wraps the assemblies 24 to form packages 25, and folds the packages 25 into pouches 26. All three operations are performed on an in-line process, without interrupting assembly conveyance and without reversing the direction of assembly conveyance. Referring first to FIG. 11, the system 100 includes as its principal components: an assembly former 102, a longitudinal folder 104, a seal and cut mechanism 106, and a two-stage folder 108. Components other than the two-stage folder 108 are identical or similar to the same or similar components used in similar processes known to those skilled in the art. These components therefore will be discussed only briefly and primarily by way of their function.

The assembly former 102 receives pre-formed napkins 20 and a continuous sheet of wrapper material 22' and applies the three garment adhesive strips 46, 48 and 50 to the continuous sheet of wrapper material 22' to form assemblies 24 connected end-to-end. The napkins 20 are then positioned on the continuous sheet of wrapper material 22' and the two members 22' and 20 are secured together by the garment adhesive 46, 48, and 50. In FIG. 11, the napkins 20 and continuous sheet of wrapper material 22' are fed into the assembly former 102 from above and below, respectively, by first and second conveyors 110 and 112. The first conveyor 110 can be a vacuum conveyor 110 having a downwardly-facing conveying surface. The second conveyor 112 can be a roller-driven belt conveyor disposed beneath the discharge end of the first conveyor 110 and having an upwardly-facing conveying surface. A standard adhesive applicator 114 applies the first, second and third garment adhesive strips 46, 48 and 50 to the continuous sheet of wrapper material 22' as the continuous sheet of wrapper material 22' is fed into the assembly former 102 by the second conveyor 112. Alternatively, the adhesive strips 46, 48 and 50 could be applied onto the napkins 20. The speeds of the conveyors 110 and 112 are coordinated in a known manner so that the first, second, and third garment adhesive strips 46, 48 and 50 register at the proper locations of a corresponding napkin 20. Assembly formation is completed by a conventional press roller 116 which presses the napkins 20 onto the continuous sheet of wrapper material 22' to set the pressure-sensitive garment adhesive strips 46, 48, and 50. It should be understood that the orientation of the assembly former 102 could be reversed so that the napkins 20 are fed into the assembly former 102 from below and so that the continuous sheet of wrapper material 22' is fed into the assembly former 102 from above. In this case, the vacuum conveyor 110 would be replaced by a conventional belt conveyor or the like.

Still referring to FIG. 11, the longitudinal folder assembly 104 folds the side flaps 56 and 58 of the continuous sheet of wrapper material 22' over the napkin topsheets 36. In the illustrated and preferred embodiment, the longitudinal folder assembly 104 includes an adhesive applicator 124 and a folding plow disposed over a discharge portion of the conveyor 112. The plow includes a pair of curved plow blades 126 and 128 that engage and fold the lateral opposed edges of the continuous sheet of wrapper material 22'. Specifically, as the continuous sheet of wrapper material 22' is conveyed to the left as viewed in the drawings, the plow blades 126 and 128 engage the side edges of the continuous sheet of wrapper material 22' forming the side flaps 56 and 58 and fold them longitudinally about the fold lines 52 and 54 in FIGS. 2 and 4 to create a package as described above. The plow blades 126 and 128 are staggered in the direction of sheet conveyance so that the two side flaps 56 and 58 are folded without interfering with one another, i.e., so that they are folded one on top of the other to form a seam in the vicinity of the longitudinal centerline X—X of the assemblies 24 (FIG. 3). The adhesive applicator 124 applies the above-described frangible adhesive strips 60 to the overlap or seam area of the first flap 56, and the second or opposing flap 58 is pressed by the second plow blade 128 into sealing contact with these adhesive strips 60. As noted above, these adhesive strips are not critical to assembly wrapping, and they could be replaced with tape or a thermal bond.

Three-dimensional vacuum conveyors could be used in combination with the plow blades 126 and 128. These conveyors would follow the contour of the plow blades 126 and 128 so that the side flaps 56 and 58 travel between the conveyors and the plow blades 126 and 128 under the guidance of the conveyors. Such conveyors would complicate the process, but would enhance process reliability and permit higher production rates. The use of three-dimensional vacuum conveyors in conjunction with folders is well-known to those skilled in the art, and a detailed description of conveyors suitable for this process therefore will be omitted for the sake of brevity.

Still referring to FIG. 11, the product leaving the longitudinal folder assembly 104 consists of a continuous string of packages 25 attached one to the other in an end-to-end fashion. The seal and cut assembly 106 then cuts the continuous sheet of wrapper material 22' between adjacent packages to form the individual packages 25, and seals the ends 69 and 71 of these packages 25 to fully-enclose the napkins 20 within the packages 25 like sausages. Seal and cut assemblies suitable for these purposes are well known to those skilled in the art. The typical such assembly includes a pair of spaced apart heated seal/cut rollers 136, 138. The lower roller 138 has a plurality of circumferentially spaced "anvils" each of which has an axially extending central glue applicator. As each anvil rotates in contact with the continuous sheet of wrapper material 22', the continuous sheet of wrapper material 22' is cut by the anvil, the applicator thermally bonds or otherwise seals the ends 69 and 71 of the now-separated and adjacent packages 25 while the anvil and mating roller 136 compress the sealed package ends 69 and 71. Individually wrapped and sealed packages 25 are formed at this time.

It should be noted that if the napkins 20 are fed into the process from below rather than from above, the downstream portion of the illustrated conveyor 112 would be replaced by a vacuum bed located above the packages 25, and the longitudinal folder assembly 104 would be placed beneath the vacuum box.

Still referring to FIG. 11, a flipper mechanism 140 is positioned downstream of the seal and cut assembly 106 for inverting the newly-formed packages 25 so that they are conveyed into the two-stage folder assembly 108 with their seams facing downwardly. The illustrated flipper mechanism 140 takes the form of a curved plate located immediately downstream of the seal and cut rollers 136 and 138. The packages 25 turn over as they slide over the concave surface of the plate and then are deposited in their inverted position on a downstream infeed conveyor 150 of the two-stage folder assembly 108. The flipper mechanism 140 could be replaced by twist belts of known construction or by any other suitable mechanism capable of turning the packages 25 180°. The flipper mechanism 140 also could be eliminated if the orientations of the conveyors 110 and 112 for the napkins 20 and continuous sheet of wrapper material 22' were to be inverted as described above or if the orientation of the two-stage folder assembly 108 were to be inverted as described below.

The two-stage folder assembly 108 ti-folds the packages 25 to form completed e-shaped pouches 26. Still referring to FIG. 11, the two-stage folder assembly 108 includes a first or infeed conveyor 150, first and second pusher assemblies 152 and 154, an adhesive applicator 156, and a second or outfeed conveyor 158.

The infeed conveyor 150 conveys the individually wrapped but not-yet folded packages 25 to the pusher assemblies 152 and 154 in a spaced-apart relationship. The speed of the conveyor 150 is controlled to match the speed of the pusher assemblies 152 and 154.

Still referring to FIG. 11, the pusher assemblies 152 and 154 reciprocate vertically and horizontally, respectively, to fold assemblies 24 into pouches 26. The pusher assemblies 152 and 154 may be reciprocated by cams, hydraulic cylinders, or the like. In the preferred embodiment, they are reciprocated by respective pneumatic cylinders 160 and 162. Each pusher assembly 152 or 154 has a flat pusher plate 164 or 166 attached to the rod end of the associated cylinder 160 or 162. Each pusher plate 164 or 166 should be at least as wide as the width of a package 25. A longitudinal slot 168, 170 is formed in the free end of each pusher plate 164, 166 for reasons which will become apparent below. The leading edge of each of the pusher plates 164 and 166 preferably is tapered or presents a radius so as to reduce the pressure imposed upon the packages 25 during pushing operations and to inhibit assembly cutting or slicing. The pusher plates 164, 166 also should be formed of a low friction material and/or treated with silicon or another friction reducing agent to facilitate assembly folding.

Figure 15:
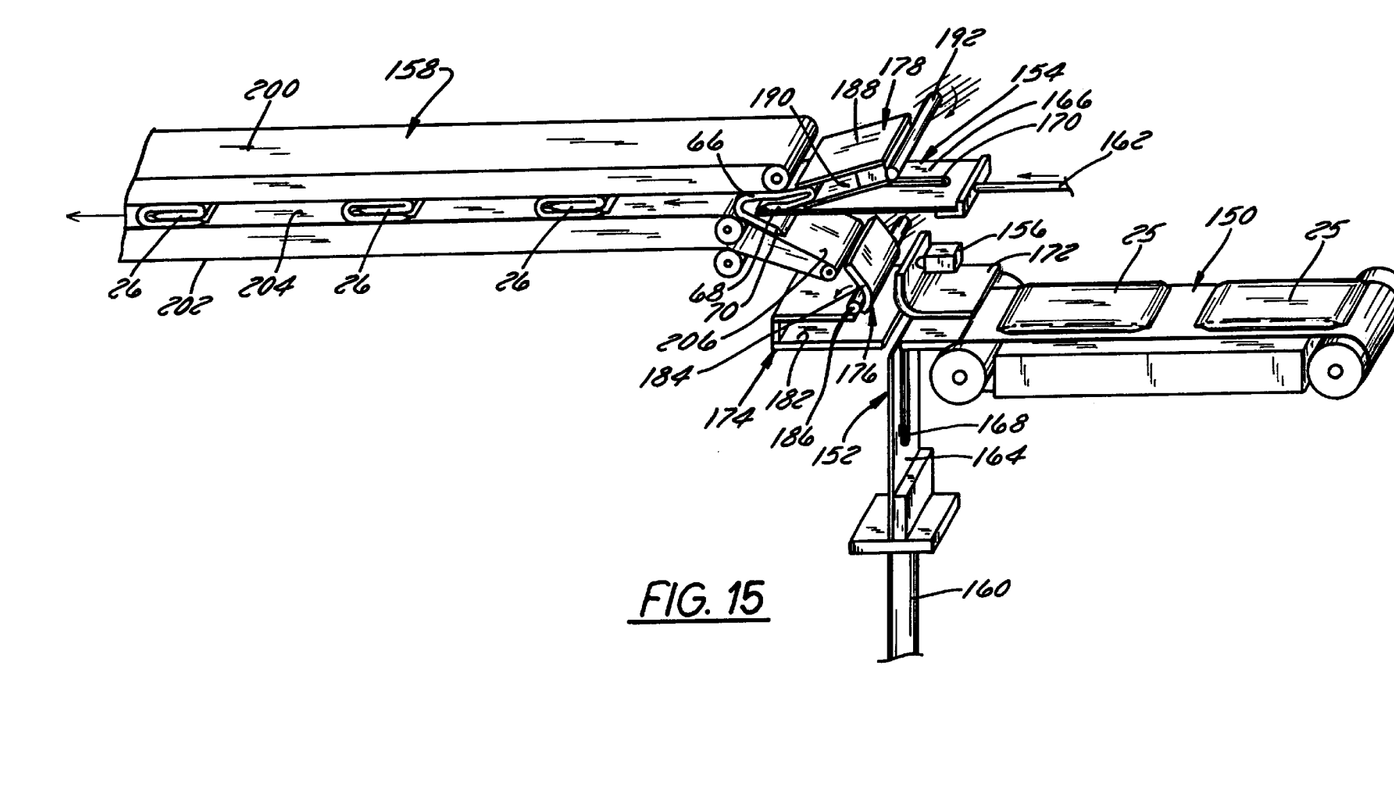
FIG. 15 corresponds to FIGS. 12 and 13 and illustrates the two-stage folder assembly in a sequence of operation in which a second longitudinal flap of the pouch is folded over the first longitudinal flap.

Guides are incorporated into the two-stage folder assembly 108 to direct movement of the packages 25 through the pusher assemblies 152 and 154 and to assist in the folding operation. These guides include first and second stationary guides 172 and 174 and first and second pivoting guides 176 and 178. The first stationary guide 172 comprises a curved plate which has a horizontal leg spaced above the discharge end of the infeed conveyor 150 and a vertical leg which extends upwardly from the discharge end of the infeed conveyor 150. The second stationary guide 174 comprises a C-shaped frame presenting a socket 182 (FIGS. 12–15) which faces the discharge end of the infeed conveyor 150 with a short gap therebetween of sufficient thickness to receive the pusher blade 164. The socket 182 receives the leading edges of conveyed packages to prevent them from overshooting the pusher assembly 152. The first pivoting guide 176 comprises a curved plate 184 which is spaced from the first stationary guide 172 to present an assembly-receiving gap therebetween. The plate 184 curves upwardly and to the left in the drawings and is pivotable with a pivot pin 186 from a generally vertical orientation (FIGS. 11 and 12) to an orientation in which its upper end is positioned adjacent the entrance of the outfeed conveyor 158 (FIG. 15). The second pivoting guide 178 comprises a C-shaped frame 188 which presents a socket 190 (FIGS. 12–13 and 15) and which is pivotable with a pivot pin 192 from a generally vertical orientation (FIGS. 11 and 12) to an orientation in which its lower end is positioned adjacent the entrance of the outfeed conveyor 158 (FIG. 15).

Figures 13, 14:
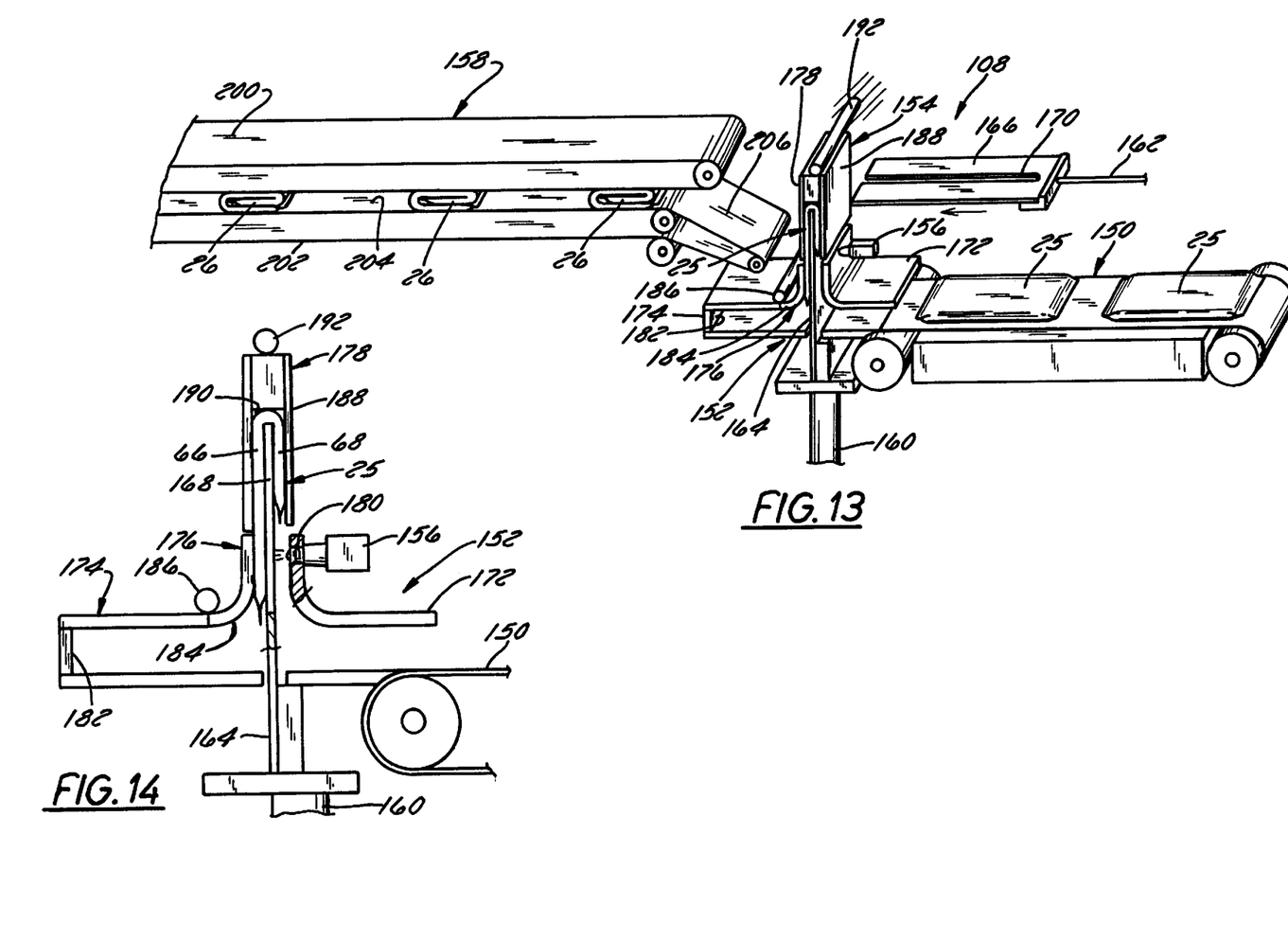
FIG. 13 corresponds to FIG. 12 except that it illustrates the two-stage folder assembly in a second stage of its sequence of operation with a cylinder being moved to an up position in which a first reciprocating pusher of the two-stage folder assembly folds a first longitudinal flap of the pouch over a central portion of the pouch.
FIG. 14 is a partially sectional side elevation view of a portion of the two-stage folder assembly of FIGS. 12 and 13 and showing application of an adhesive to the pouch.

As best seen in FIG. 14, the adhesive applicator 156 is mounted on a laterally central portion of the vertical leg of the first stationary guide 172 so as to be capable of injecting adhesive through an orifice 180 in the guide 172, through the slot 168 of the pusher plate 164, and onto a package 25 being driven by the pusher plate 164. This applicator 156 could, however, be replaced by a tape applicator or some other suitable structure.

Referring again to FIG. 11, the outfeed conveyor 158 is formed from a pair of spaced-apart continuous belt conveyors 200 and 202. The conveyors 200 and 202 convey pouches 26 away from the pusher assemblies 152 and 154 while compressing the pouches 26 in a nip 204 formed between the conveyors 200 and 202 to reduce their overall thickness and to press the adhered flaps 68 and 70 of each pouch 26 into sealing engagement at the locations of the adhesive patch 72. The lower conveyor 202 includes an upwardly-inclined entrance section 206 which receives pouches 26 from the pusher assembly 154 and which feeds the pouches 26 into the nip 204.

Figure 12:
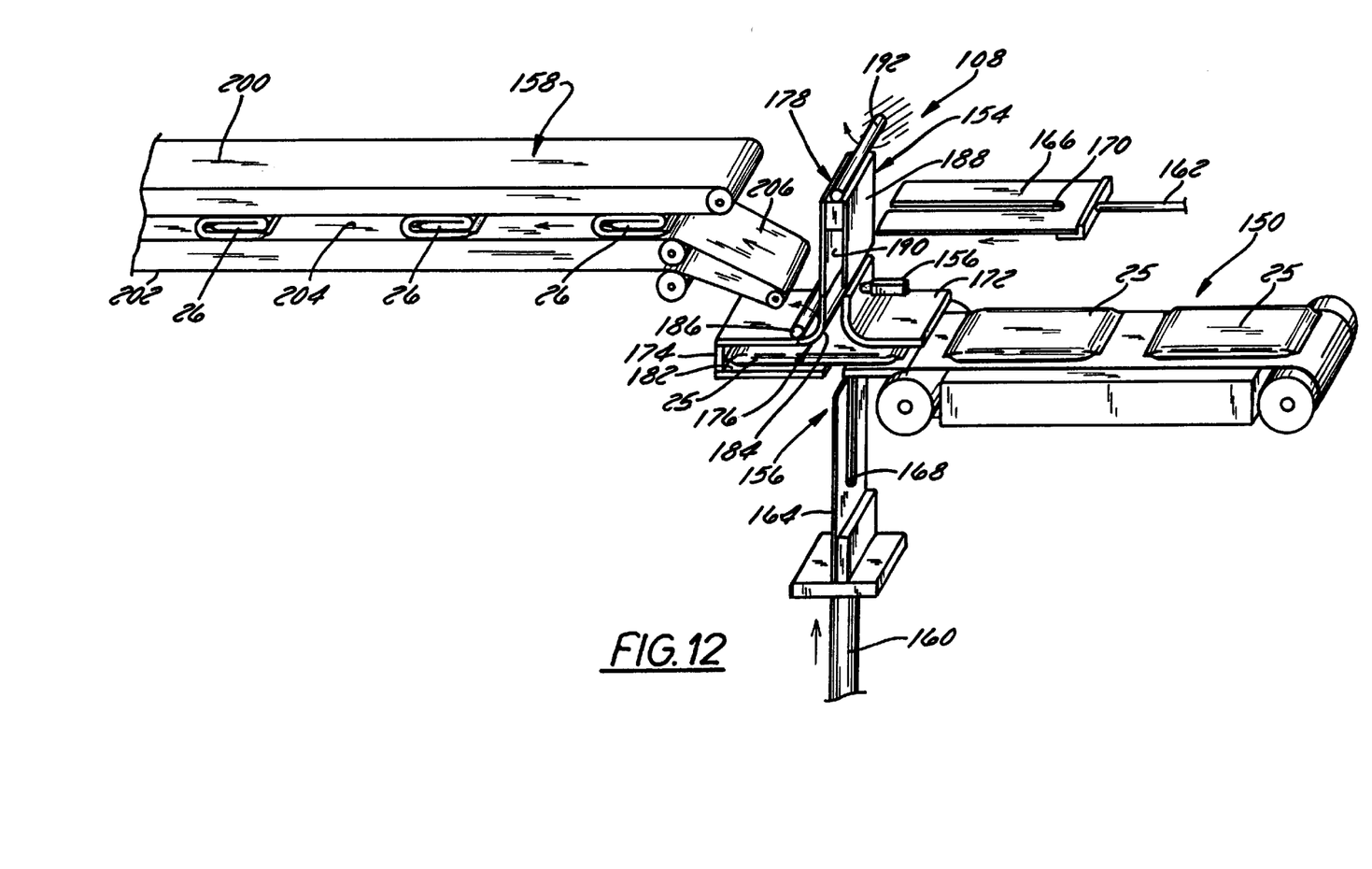
FIG. 12 is a partially schematic perspective view illustrating a two-stage folder assembly of the system depicted in FIG. 11 and illustrates a first stage of its sequence of operation in which a package is positioned for folding into a pouch by the two-stage folder assembly.

Pouches 26 are formed in the two-stage folder assembly 108 as follows:

Referring to FIG. 12, packages 25 are fed into the two-stage folder assembly 108 from the infeed conveyor 150 with the longitudinal seams (formed by the overlapping portions of the side flaps 56 and 58) facing downwardly. As a package 25 enters the two-stage foler assembly 108, the pusher plate 164 of the first pusher assembly 152 is driven upwardly by its pneumatic cylinder 160 so as to engage the package 25 near the lateral fold line 62. Continued upward movement of the pusher plate 164 lifts the package 25 from the plane of the infeed conveyor 150 so that the package 25 is forced between the curved guides 172 and 176 as illustrated in FIG. 13, thereby partially folding the first longitudinal flap 68 over the central portion 66. The adhesive applicator 156 is activated at this time as illustrated in FIG. 14 to spray a patch 72 of adhesive (FIGS. 4 and 5) through the slot 168 of the first pusher plate 164 and onto the end of the second longitudinal flap 70. Continued upward movement of the first pusher plate 164 forces a portion of the package 25 comprising the junction of the central portion 66 and the first longitudinal flap 68 into the socket 190 of the second pivoting guide 178 as illustrated in FIGS. 13 and 14.

Movement of the partially-folded, now U-shaped package 25 into the socket 190 further folds the first longitudinal flap 68 over the central portion 66 and the first pusher plate 164.

Next, movement of the first pusher assembly 152 is reversed to retract the first pusher plate 164 form the socket 190, and the second pusher assembly 154 is extended to drive the second pusher plate 166 towards the second pivoting guide 178. Metal-to-metal contact between the pusher plate 166 and the guide 178 could be eliminated by mechanically coupling the pivot pin 192 to the pusher assembly 154 by a pivot linkage, cam, or the like (not shown). The guide 178 then would pivot without being contacted by the pusher plate 166.

As the pusher plate 166 continues to extend, it moves along the guide 178 and into contact with the package 25 at a location adjacent the lateral fold line 64 between the central portion 66 and the second flap 70 as seen in FIG. 15. Continued movement of the pusher plate 166 pushes the package 25 out of the socket 190 and towards the outfeed conveyor 158. During this motion, the second longitudinal flap 70 of the package 25 engages the first pivoting guide 176 and begins to fold over the first longitudinal flap 68 (thereby forming a pouch 26) while it forces the guide 176 to pivot to the position illustrated in FIG. 15. The slot 170 in the second pusher plate 166 is aligned with the adhesive patch 72 on the second flap 70 at this time so that the pusher plate 166 does not smear the adhesive patch 72. Additional pusher plate movement forces the pouch 26 onto the upwardly-inclined entrance section 206 of the lower belt 202 of the discharge conveyor 158 to cause the second longitudinal flap 70 of the pouch 26 to bend further over the first longitudinal flap 68. The outfeed conveyor 158 then conveys the pouch 26 away from the second pusher assembly 154 and into the nip zone 204 where the pouch 26 is compressed to compact it and to set the pressure sensitive adhesive patch 72. The outfeed conveyor 158 then conveys the finished pouch 26 out of the system 100 for subsequent action such as packaging in cartons or boxes.

The above-described process can be performed more rapidly than conventional tri-folding processes because it is performed in-line, i.e., package transfer does not have to cease or reverse directions during the folding process. In addition, because the process does not require the operation of any conventional folding blades, there is little danger of piercing the pouch during the folding process.

Many changes and modifications could be made to the invention without departing from the spirit thereof. For instance, as mentioned previously, the invention is applicable to other absorbent articles in addition to sanitary napkins. Moreover, and within the described embodiments, the adhesive patch 72 could be eliminated or could be replaced by a strip of adhesive tape. The applicator 156 that applies the adhesive patch 72 could also be placed in a different location in the system 100, e.g., upstream of the two-stage folder assembly 108, and a separate heated or ultraviolet activator could be located downstream of the two-stage folder assembly 108 to set the adhesive. In addition, the two-stage folder assembly 108 could be inverted so that the outfeed conveyor 158 is located beneath the infeed conveyor 150 and so that the first pusher assembly 152 forces the packages 25 downwardly rather than upwardly as illustrated. Moreover, as discussed above, the illustrated wrapping and folding system could be replaced by a variety of other systems, or wrapping and folding could even be performed manually. The scope of other changes will become apparent from the appended claims.

I claim:

1. A system for folding packages, wherein the system is characterized as including:
   (a) a first conveyor adapted to convey packages, each package having a leading edge and a trailing edge, each package characterized as including a wrapper and an absorbent article secured to said wrapper;
   (b) a first, vertically reciprocating pusher adapted to receive said packages from said first conveyor, each package being received leading edge first, said first pusher operating to partially-fold each of said packages proximate to a respective trailing edge;
   (c) a second, horizontally reciprocating pusher located in a vertically-spaced relationship with respect to said first conveyor and said first pusher and which is adapted to receive each of said packages from said first pusher and to further fold each of said packages, thereby to form e-shaped pouches; and
   (d) a second conveyor located in the vicinity of the second pusher and adapted to receive the e-shaped pouches from the second pusher.

2. The system of claim 1, further characterized as including:
   (a) an assembly former which releasably secures absorbent articles to a continuous sheet of wrapper material, thereby to form assemblies;
   (b) a longitudinal folder which is located downstream of said assembly former and which folds said continuous sheet longitudinally over said absorbent articles; and
   (c) a cutter which is located downstream of said longitudinal folder and which cuts said continuous sheet between adjacent ones of said absorbent articles, thereby to form said packages.

3. The system of claim 1 wherein the second conveyor is a pair of conveyors comprised of an upper belt conveyor and a lower belt conveyor, substantially parallel and proximally spaced apart.

4. The system of claim 3 wherein said lower conveyor includes an upwardly inclined entrance section.

5. The system of claim 1, further comprising:
   a pivotable socket vertically positioned to temporarily receive each of said packages and maintain said respective first partial fold created by the first pusher;
   further wherein said second pusher is adapted to receive each of said packages from said pivotable socket; and
   wherein the second conveyor is adapted to receive the pouches from the second pusher via the pivotable socket.

6. The system of claim 5 wherein said first and second pushers are slotted to permit application of an adhesive to said packages without interference from said first and second pushers.

7. A system for folding packages, wherein the system is characterized as including:
   (a) a first conveyor adapted to convey packages characterized as including a wrapper and an absorbent article secured to said wrapper;
   (b) a first, vertically reciprocating pusher adapted to receive said packages from said first conveyor and to partially-fold said packages;
   (c) a second, horizontally reciprocating pusher located in a vertically-spaced relationship with respect to said first conveyor and said first pusher and which is adapted to receive said packages from said first pusher and to further fold said packages, thereby to form pouches; and
   (d) a second conveyor located in the vicinity of the second pusher and adapted to receive the pouches from the second pusher; and
   wherein said first and second pushers are slotted to permit application of an adhesive to said packages without interference from said first and second pushers.

8. A method for tri-folding packages, comprising the steps of:
   placing the packages on a first conveyor, wherein the packages each have a leading edge and a trailing edge,
   conveying the packages, leading edge first, to a first, vertically reciprocating pusher,
   operating the first, vertically reciprocating pusher to partially-fold each of the packages proximate to a respective trailing edge, operating a second, horizontally reciprocating pusher to further fold each of the packages to form a pouch, wherein the second pusher is located in a vertically spaced relationship with respect to the first conveyor and the first pusher, and
   receiving the pouches by a second conveyor located in the vicinity of the second pusher.

9. The method of claim 8 further comprising a step for applying an adhesive, wherein the first pusher and the second pusher are slotted to permit application of the adhesive without interference from the first pusher and the second pusher.

10. The method of claim 8 further comprising a step for compressing the packages by the second conveyor following the folding step of the second pusher.

11. The method of claim 10 wherein said second conveyor is a pair of conveyors comprised of an upper belt conveyor and a lower belt conveyor substantially parallel and proximally spaced.

* * * * *